(12) United States Patent
Garcia-Rill (10) Patent No.: US 9,289,403 B2
(45) Date of Patent: Mar. 22, 2016

(54) USE OF MODAFINIL TO TREAT SPASTICITY

(75) Inventor: Edgar Garcia-Rill, Little Rock, AR (US)

(73) Assignee: The Board of Trustees of the University of Arizona, Little Rock, AZ (US)

( * ) Notice: Subject to any disclaimer, the term of this patent is extended or adjusted under 35 U.S.C. 154(b) by 1948 days.

(21) Appl. No.: 11/716,218

(22) Filed: Mar. 9, 2007

(65) Prior Publication Data

US 2008/0221216 A1 Sep. 11, 2008

(51) Int. Cl.
*A61K 31/165* (2006.01)

(52) U.S. Cl.
CPC ................................. *A61K 31/165* (2013.01)

(58) Field of Classification Search
CPC .................................................. A61K 31/165
See application file for complete search history.

(56) References Cited

U.S. PATENT DOCUMENTS

| 4,177,290 A | 12/1979 | Lafon |
| 4,927,855 A | 5/1990 | Lafon |

OTHER PUBLICATIONS

Urbano et al. "Modafinil enhances thalamocortical ctivity by increaseing neuronal electrotonic coupling" PNAS, Jun. 14, 2007 (internet publishing date), vol. 104, No. 30, pp. 12554-12559.*
Dietz et al. "Degradation of neuronal function following a spinal cord injury: mechanisms and countermeasures" Brain, 2004, vol. 127, pp. 2221-2231.*
Classen et al. "The timing of prophylactic administration of antibiotics and the risk of surgical-wound infection" New England Journal of Medicine, Jan. 30, 1992, vol. 326, pp. 281-286.*
Medtronic, Inc "Intrathecal Baclofen therapy for treating cerebral palsy cleared by FDA", Doctor's guide, Jun. 19, 1996, http://ww.pslgroup.com/dg/9946.htm.*
Reese et al. "Restoration of frequency-dependent depression of the H-reflex by passive exercise in spinal rats" Spinal Cord, 2006 (published online Jul. 26, 2005), vol. 44, pp. 28-34.*
Hurst, DL et al. Us of modafinil in spastic cerebral palsy. J. Child Neurol. 2002; 17:169-172.
Katz R, Rymer W. Spastic hypertonia: mechanisms and measurement. Arch Phys Med Rehabil 1989; 70: 144-155.
Angel RW, Hofmann WW. The H-reflex in normal, spastic, and rigid subjects. Arch Neurol 1963; 8: 591-596.
Little JW, Halar EM. H-reflex changes following spinal cord injury. Arch Phys Med Rehab 1985; 66: 19-22.
Calancie B et al. Evidence that alterations in presynaptic inhibition contribute to segmental hypo- and hyperexcitability after spinal cord injury in man. Electroencephalogr and Clin Neurophysiol 1993; 89: 177-186.
Schindler-Ivens S, Shields RK. Low frequency depression of H-reflexes in humans with acute and chronic spinal-cord injury. Exp Brain Res 2000; 133: 233-241.
Chen XY, Feng-Chen KC, Chen L, Stark DM, Wolpaw JR. Short-term and medium-term effects of spinal cord tract transactions on soleus H-reflex in freely moving rats. J Neurotrauma 2001; 18: 313-327.
Thompson FJ, Reier PJ, Lucas CC, Parme R. Altered patterns of reflex excitability subsequent to contusion injury of the rat spinal cord. J Neurophysiol 1992; 68: 1473-1486.
Olsen PZ, Diamantopoulos E. Excitabiliity of spinal motor neurons in normal subjects and patients with spasticity, Parkinsonian rigidity, and cerebellar hypotonia. J Neurol Neurosurg Psychiatry 1967; 30: 325-331.
Bennett DJ, Li Y, Harvey PJ, Gorassini M. Evidence for plateau potentials in tail motoneurons of awake chronic spinal rats with spasticity. J Neurophysiol 2001; 86: 1972-1982.
Li Y, Bennett DJ. Persistent sodium and calcium currents cause plateau potentials in motoneruons of chronic spinal rats. J Neurophysiol 2003; 90: 857-869.
Li Y, Li X, Harvey PJ, Bennett DJ. Effects of baclofen on spinal reflexes and persistent inward currents in motoneurons of chronic spinal rats with spasticty. J Neurophysiol 2004; 92: 2694-2703.
Hultborn H. Changes in neuronal properties and spinal reflexes during development of spasticity following spinal cord lesions and stroke: studies in animal models and patients. J Rehab Med 2003; S41: 46-55.
Skinner RD, Houle JD, Reese NB, Berry CL, Garcia-Rill E. Effects of exercise and fetal spinal cord implants on the H-reflex in chronically spinalized adult rats. Brain Res 1996; 729: 127-131.
Dachy B, Dan B. Electrophysiological assessment of the effect of intrathecal baclofen in spastic children. Clin Neurophysiol. 2002; 113(3):336-40.
Bakheit AM, Maynard VA, Curnow J, Hudson N, Kodapala S. The relation between Ashworth scale scores and the excitability of the alpha motor neurones in patients with post-stroke muscle spasticity. J Neurol Neurosurg Psychiatry. 2003; 74(5):646-8.
Sadowsky CL. Electrical stimulation in spinal cord injury. Neurorehabilitation 2001; 16: 165-169.
Barbeau H, Norman KE. The effect of noradrenergic damage on the recovery of walking after spinal cord injury. Spinal Cord 2003; 41: 137-143.
Walton KD, Navarrete R. Postnatal changes in motoneurone electrotonic coupling studied in the in vitro rat lumbar cord. J Physiol 1991; 433: 283-305.
Laudau WM, Clare MH. Fusimotor function. VI. H-reflex, tendon jerk and reinforcement in hemiplegia. Arch Neurol Psychiat 1964; 10: 128-134.
Murphy, AM et al. 2008. Impact of modafinil on spasticity reduction and quality of life in children with CP. *Dev. Med. Child Neurol.* 50:510-514.
Hayar, A. et al., Oocyte triplet pairing for electrophysiological investigation of gap junctional coupling, 2010, *J. Neuroscience Methods* 188:280-286.

* cited by examiner

*Primary Examiner* — Kendra D Carter
(74) *Attorney, Agent, or Firm* — Hugh McTavish (57) ABSTRACT

The invention provides a method of reducing spasticity in a mammal involving administering modafinil or related compounds. The spasticity can be secondary to multiple sclerosis, spinal cord injury, stroke, brain injury, and other causes.

15 Claims, 7 Drawing Sheets

USE OF MODAFINIL TO TREAT SPASTICITY

GOVERNMENT SUPPORT

This invention was made with government support under grant RR20146 awarded by the United States National Center for Research Resources. The government has certain rights in the invention.

BACKGROUND

Spasticity is a disorder in which certain muscles are continuously contracted. Symptoms include exaggerated reflexes (hyper-reflexia), muscle spasms and fixed joints. Spasticity is difficult to quantify because of its various components, however, most researchers quantify its major component, hyper-reflexia. Spasticity may be as mild as a feeling of tight muscles, or may so severe as to produce uncontrollable, painful spasms of the legs or other extremities. Spasticity can interfere with movement and speech. Untreated spasticity can lead to frozen or immobilized joints and pressure sores. It prevents recovery of proper motor behavior after injury or disease.

Spasticity can arise as a consequence of several conditions including spinal cord injury (SCI), stroke, cerebral palsy, brain injury and multiple sclerosis. Spasticity in patients with SCI is particularly difficult to manage. Exercise and stretching are advocated as management tools, but these activities are difficult to perform for most patients. The patients often do not appreciate the long-term benefits from stretching and exercise, an effective stretching or exercise program takes time to perform, and individuals with paraplegia or tetraplegia often need assistance to perform such a program. These same barriers also often exist for other patients with spasticity, including stroke victims, brain injury victims, cerebral palsy patients and multiple sclerosis patients.

Drugs available for the management of spasticity include baclofen. Baclofen is a GABAb receptor agonist. Baclofen basically acts to potentiate inhibition mediated by presynaptic GABAb receptors. The rationale for the use of baclofen for the treatment of spasticity was due to the assumption that excessive reflexes were induced in SCI by the elimination of presynaptic inhibition from nerve fibers descending from the brain. SCI has been thought to lesion these descending fibers, rendering the spinal cord hyper-reactive. Baclofen is thought to restore some of that inhibition. However, baclofen taken orally unfortunately increases inhibition throughout the brain, leading to sleepiness and weakness. In order to avoid such side effects (which reduce the ability of patients to concentrate), baclofen pumps were designed to inject the drug directly into the spinal fluid, usually in SCI victims and cerebral palsy patients. These pumps avoid the soporific effects of oral administration but are dangerous, have a limited lifetime (requiring repeated surgical implants) and are very expensive.

New treatments for spasticity are needed.

SUMMARY OF THE INVENTION

The invention involves the discovery that modafinil, an approved drug for the treatment of narcolepsy, is effective to treat spasticity in spinal cord-injured subjects. Modafinil and related compounds can be used to treat spasticity from other conditions also, including stroke, multiple sclerosis, and brain injury.

Previous studies in our laboratories showed that the excessive reflexes induced by SCI (as quantified by measurement of the habituation of the Hoffman or H-reflex, the electrical equivalent of the tendon tap reflex) could be reduced and even abolished using a passive exercise regimen. SCI is known to reduce the habituation of this reflex to repetitive stimulation, thus leading to excessive reflex responses and promoting spasticity. The normalization of excessive reflexes, determined by restoration of normal habituation of the H-reflex, thus eliminates a major cause of spasticity. We show herein that oral administration of modafinil can also reduce or block the excessive reflexes produced by SCI (as measured using H-reflex habituation), even without an exercise program.

Modafinil thus may be used for the treatment of spasticity and excessive reflexes produced by any condition, including SCI, stroke, cerebral palsy, brain injury and multiple sclerosis.

One embodiment of the invention provides a method of treating spasticity in a mammal involving administering to the mammal a dose of a compound of formula I or a pharmaceutically acceptable salt thereof effective to reduce hyper-reflexia in the mammal; wherein the spasticity is not secondary to cerebral palsy:

In the compound of formula I each of rings a and b may optionally be substituted by one or more of the groups F, Cl, Br, $CF_3$, $NO_2$, $NH_2$, $C_{1-4}$alkyl, $C_{1-4}$alkoxy, and methylenedioxy. Z is >CHSO— or >NCO—. A is hydrogen; $C_{1-4}$alkyl; $C_{1-4}$hydroxyalkyl; a group of the formula —Y— $NR_2$, wherein Y is a divalent linear or branched chain $C_{1-4}$hydrocarbon radical and each R is independently H or $C_{1-4}$alkyl; or a hetercyclic group that has five to seven ring members, including one or two heteroatoms selected from N and O, and optionally substituted with 1 or 2 $C_{1-4}$alkyl.

Another embodiment of the invention provides a use of a compound of formula I to prepare a medicament effective to reduce hyper-reflexia associated with spasticity in a mammalian subject.

BRIEF DESCRIPTION OF THE DRAWINGS

FIG. 1. Averages of H-reflex recordings in intact, spinal cord injured, and spinal cord injured and exercised rats. Evoked muscle potentials included an early M-wave and a later H-reflex following stimulation. (a) Averaged responses to stimulation at 0.2 Hz in a CONTROL mammal (rat). (b) Averaged responses to stimulation at 10 Hz in the same CONTROL animal. Note the decrease in amplitude (frequency-dependent depression) of the H-reflex at 10 Hz compared to 0.2 Hz. (c) Averaged responses to stimulation at 0.2 Hz in a Tx only 60D rat (60 days after spinal cord transection without treatment). (d) Averaged responses to stimulation at 10 Hz in the same Tx ONLY 60D rat. Note the greater amplitude (decrease in frequency-dependent depression) of the H-reflex at this frequency compared to 10 Hz in the intact animal (b). (e) Averaged responses to stimulation at 0.2 Hz in a Tx+Ex 60D rat (transected and then exercised for 60 days). (f) Averaged responses to stimulation at 10 Hz in the same Tx+Ex 60D rat. Note the return of frequency-dependent depression of the H-reflex after 60 days of MBET. Calibration bars vertical 0.5 mV, horizontal 2 ms. These results show that a passive exercise regimen can eliminate the excessive reflexes caused by SCI (spinal transection in this case).

FIG. 2. Averages of H-reflex recordings in intact, spinal cord injured, and rats spinal cord injured and exercised for various durations. H-reflex amplitude at 0.2, 1, 5, and 10 Hz for intact animals (CONTROL, open circles), and 15 (Tx+Ex 15D, filled diamonds), 30 (Tx+Ex 30D, filled circles), 45 (Tx+Ex 45D, filled triangles), 60 (Tx+Ex 60D, filled plus signs) and 90 (Tx+Ex 90D, filled squares) days of MBET, and 90 days without MBET (Tx ONLY 90D, open squares). Frequency-dependent depression of the H-reflex at 0.2 Hz was designated 100%, and all statistical comparisons in this figure made against the Tx only 90D group. At 1 Hz, the Tx only 90D group (*) differed significantly from the Tx+Ex 45D, Tx+Ex 60D, and CONTROL groups at the P<0.05 level (+); and from the Tx+Ex 30D group at the P<0.01 level (++). At 5 Hz, the Tx only 90D group (*) differed from the Tx+Ex 45D, and Tx+EX 60D groups at the P<0.05 (+), and was also different (**) from the Tx+Ex 30D and CONTROL group at the P<0.01 level (++). At 10 Hz, the Tx only 90D group (*) differed from the Tx+Ex 45D group at the P<0.05 level (+), and differed (**) from the Tx+Ex 30D, Tx+Ex 60D, Tx+Ex 90D, and CONTROL groups at the P<0.01 level (++). These results show that exaggerated reflexes are normalized by increasing the duration of passive exercise.

FIG. 3. Averages of H-reflex recordings in intact, spinal cord injured and studied 30 days after, and rats spinal cord injured and exercised for 30 days. H-reflex amplitude at 0.2, 1, 5, and 10 Hz for CONTROL (open circles), 30 days without MBET (Tx only 30D, filled squares), and 30 days with MBET (Tx+Ex 30D, filled diamonds). Frequency-dependent depression of the H-reflex at 0.2 Hz was designated 100%, and all statistical comparisons in this figure made against the Tx ONLY 30D group. At 1 Hz, the Tx only 30D group (*) differed from the Tx+Ex 30D group at the P<0.05 level (+), but not the CONTROL group. At 5 Hz, the Tx only 30D group (*) differed from the Tx+Ex 30D group at the P<0.05 level (+) and from the CONTROL at the P<0.01 level (++). At 10 Hz, the Tx only 30D group (*) differed from the Tx+Ex 30 group at the P<0.05 level (+), and from the CONTROL at the P<0.01 level (++). These results show that the exaggerated reflexes present 30 days after spinal transection can be normalized by 30 days of passive exercise.

FIG. 4. Frequency-dependent habituation of the H-reflex in control and SCI human subjects. Panel A. Amplitudes of the averaged H-reflexes tested at frequencies of 1, 5, and 10 Hz are shown as a percent of the averaged H-reflex at the low-frequency (0.2 Hz) for a group of normal human subjects (solid squares, n=16) and a group of SCI subjects (open squares, n=6). The amplitudes of the H-reflex were statistically significantly different at 5 Hz (**=p<0.01). Panel B. H-reflex amplitudes of one subject who underwent motorized bicycle exercise therapy (MBET-1). Solid circles represent frequency-dependent H-reflex amplitudes before exercise began and open circles represent those recorded at week 12, at the peak of the effect of exercise on habituation of the H-reflex. These results show, in A, that SCI leads to exaggerated reflexes in humans, and in B, that passive exercise can normalize the excessive reflexes produced by SCI.

FIG. 5. Changes in H-reflex habituation at 1, 5 and 10 Hz over time in MBET-1. Frequency dependent habituation of the H-reflex over the course of 13 weeks of 5 days/week MBET sessions at 60 minutes per session, indicated by the bar at the bottom, and 4 weeks post-exercise recorded from this SCI subject. H-reflex amplitudes are shown as a percent of the H-reflex at 0.2 Hz. These results show that passive exercise must take place for weeks to months until its effects on exaggerated reflexes begins. Once normalized, if exercise is stopped, exaggerated reflexes return within a short time.

FIG. 7. Gap junction protein (connexin 36) expression in intact, transected and transected and exercised rats. Cx36 expression (mRNA) levels against 3 housekeeping genes used as internal controls (Enolase E, Gapdh G, Hprt H) in intact (Normal), transacted and analyzed 30 days after transection (Tx30D), and transected but exercised for 30 days (Tx+MBET30D). Error bars show the first and third quartiles. Bars showing expression that is significantly different from normal are shown by ++ (P<0.01) and + (P<0.05). NS indicates the difference from the normal level is not significant. These results suggest that spinal transection leads to a decrement in Cx36 gene expression and that passive exercise tends to increase such expression.

DETAILED DESCRIPTION

Definition

The term "reduce hyper-reflexia" as used herein refers to reducing the amplitude of the H-reflex measured at 1, 5, or 10 Hz as normalized to amplitude measured at 0.2 Hz stimulation. In other words, it refers to restoring low frequency-dependent depression of the H-reflex to closer to control levels. More preferably the H-reflex amplitude is reduced at 5 or 10 Hz, most preferably at 5 Hz.

DESCRIPTION

The invention involves the discovery that administration of modafinil decreases (normalizes) H-reflex amplitude in spinally transected rats. Humans having SCI develop spasticity, not immediately after the injury, but over a course of several weeks after the injury. Spinally transected rats are an animal model for SCI in humans. A major component of spasticity is exaggerated reflexes or hyper-reflexia. The Hoffman reflex or H-reflex is a standard measure used by investigators to quantify hyper-reflexia. It is the electrical analogue of the classic tendon jerk reflex. It is a compound electromyographic response elicited by the synaptic activation of motoneurons by muscle afferents following stimulation of muscle nerves. It can be measured as described in Section 1 of the Example below.

The H-reflex amplitude is a standard quantitative measurement that has been found to correspond to hyper-reflexia seen in spasticity (28, 40, 41).

The Example below shows that passive exercise with a motorized bicycle reduces H-reflex amplitude, and that this effect increases as the time period of daily one-hour exercise increases from 15 days to 90 days. The same effect of H-reflex amplitude decrease is seen with passive exercise in a single human SCI patient (Section 2 of the Example below).

Thirty days of daily modafinil administration to spinally transected rats without any passive exercise decreased (normalized) the H-reflex amplitude to the same extent as 30 days of exercise (Section 4 of the Example).

The most commonly used drug to treat spasticity, baclofen, is a GABAb receptor agonist and has the side effect of causing drowsiness. Modafinil in contrast does not cause drowsiness, and in fact is used to treat narcolepsy, but its mechanism of action is unknown. Thus, it appears to act by a different mechanism. In this regard, it is interesting that passive exercise, which also reduces spasticity, increases expression of the nerve gap junction protein connexin 36, which would increase gap junctions and increase electrical communication between neurons.

Other compounds that are structurally similar to modafinil and induce similar effects can also be used in the present methods to treat spasticity. These include compounds of formula I:

wherein each of rings a and b may optionally be substituted by one or more of the groups F, Cl, Br, $CF_3$, $NO_2$, $NH_2$, $C_{1-4}$alkyl, $C_{1-4}$alkoxy, and methylenedioxy;

Z is >CHSO— or >NCO—; and

A is hydrogen; $C_{1-4}$alkyl; $C_{1-4}$hydroxyalkyl; a group of the formula —Y—$NR_2$, wherein Y is a divalent linear or branched chain $C_{1-4}$hydrocarbon radical and each R is independently H or $C_{1-4}$alkyl; or a hetercyclic group that has five to seven ring members, including one or two heteroatoms selected from N and O, and optionally substituted with 1 or 2 $C_{1-4}$alkyl;

and pharmaceutically acceptable salts thereof.

This family of modafinil relatives is described in U.S. Pat. No. 4,177,290.

In particular embodiments of the compounds of formula I, Z is >CH—SO—.

In preferred embodiments, of the compound of formula I, A is hydrogen, hydroxymethyl or β-morpholinoethyl.

In modafinil, Z is >CH—SO— and A is hydrogen.

In particular embodiments of the methods of the invention the spasticity is secondary to (i.e., is a consequence of) multiple sclerosis, a spinal cord injury, a stroke, or a brain injury.

In a preferred embodiment, the spasticity is secondary to a spinal cord injury.

In particular embodiments of the invention, the spasticity is secondary to a neurological injury (i.e., an event that harms neurological tissue, including a spinal cord injury, brain trauma, and a stroke).

Where the spasticity is secondary to a neurological injury, in particular embodiments, a compound of formula I is administered after spasticity has set in, and in other embodiments before spasticity has had a chance to set in. That is, modafinil may be used to normalize excessive reflexes, a major element of spasticity, once they have manifested, as well as to prevent the onset of excessive reflexes after injury or disease but before hyper-reflexia and its attending spasticity has become manifested.

Thus, where the spasticity is secondary to a neurological injury, in particular embodiments a compound of formula I is administered initially within 16 weeks of the injury, preferably within 4 weeks of the injury, more preferably-within 1 week of the injury before spasticity fully develops in order to prevent development of spasticity. In other embodiments, the modafinil or other agent of formula I is administered initially after spasticity is developed, e.g., after about 16 weeks after the injury.

The invention is not limited to a particular mechanism of action. But in Section 4 of the Example below it is hypothesized that spasticity and hyper-reflexia develop over a period of weeks after spinal cord injury because of a decrease in expression of gap junction proteins and a resultant decrease in gap junctions in spinal neurons below the injury, and thereby a decrease in electrical coupling of these neurons. Connexin 36 is the primary gap junction protein in neurons. Section 4 of the Example below shows that connexin 36 gene expression is decreased after spinal cord injury in rats in spinal neurons below the site of the injury. Passive exercise is shown to reverse this decrease of connexin 36 expression. It is hypothesized that modafinil is effective because it increases connexin 36 gene expression and thereby increases electrical coupling of neurons.

The invention will now be illustrated by the following non-limiting Example.

EXAMPLE

Section 1

Restoration of Frequency-Dependent Depression of the H-Reflex by Passive Exercise in Spinal Rats Spinal cord injury (SCI) results in numerous deficits of the motor and sensory systems, including paralysis, anesthesia, and hyper-reflexia below the level of the lesion. Hyper-reflexia is evident in both humans and non-human animals following SCI and is a major component of spasticity. The physiological changes that have been postulated to contribute to hyper-reflexia include alpha motoneuron hyperexcitability (1, 2, 3), changes in the intrinsic properties of alpha motoneurons (4, 5, 6, 7), reduced post-activation depression of transmission from Ia fibers (8, 9), synapse growth (10), alterations in morphology of alpha motoneurons (11), and decreased presynaptic inhibition of Ia terminals (9, 12, 13, 14, 15). The time course of spinal changes after injury has been proposed to include an early postsynaptic mechanism, possibly involving an increase in excitability and/or receptor upregulation, and a late change involving presynaptic mechanisms possibly involving synaptic growth in spared descending pathways and in reflex pathways (10). One measure used by numerous investigators to quantify hyper-reflexia is the electrical analogue of the classic tendon jerk reflex, referred to as the Hoffman or H-reflex (2, 15, 16, 17, 18, 19). The H-reflex is a compound electromyographic (EMG) response elicited by the synaptic activation of motoneurons by muscle afferents following stimulation of muscle nerves. Thompson et al. investigated four measures of H-reflex excitability in a contusion model of SCI in the rat (20). Results of their studies led these researchers to conclude that rate-sensitive depression of the H-reflex was of particular importance in the assessment of hyper-reflexia following SCI. Other groups have reached similar conclusions regarding the importance of changes in H-reflex rate-sensitive depression as a measure of the effects of SCI (21). In spinally intact individuals, the H-reflex demonstrates depressed amplitude, due to marked frequency-dependent depression, once stimulus frequencies reach or exceed 1 Hz (22, 23). However, frequency-dependent depression of the H-reflex is less evident in patients or animals with chronic SCI (12, 13, 22, 24, 25). The present section of this Example reports on a study to determine the effect of passive exercise therapy to restore frequency-dependent depression of the H-reflex in adult rats with complete spinal cord transections. A motorized bicycle was used to provide the passive exercise (motorized bicycle exercise training (MBET)).

Methods

Surgery

Adult female Sprague-Dawley rats (Harlan, 200-250 g, n=40) underwent a lower thoracic laminectomy under ketamine (60 mg/kg, i.m.) and xylazine (10 mg/kg, i.m.) anesthesia. A complete transection (Tx) of the spinal cord was made by aspiration and the transected ends of the cord retracted, producing a 2-3 mm cavity. Gelfoam was inserted into the cavity to facilitate hemostasis and the dura was closed over the Tx site. Muscle and skin were sutured in separate layers, and animals were provided with dextrose-saline (5%, 1 ml/100 g body weight, s.c.) to replace fluid lost during the surgical procedure. Penicillin (5000 U, i.m.) was administered immediately postoperatively, and animals were transferred to an incubator maintained at 37.5° C. until fully recovered from the anesthetic. The urinary bladder of each animal was expressed manually twice daily until reflexive voiding was established (10-14 days). Animals were monitored for signs of urinary tract infection, and treatment with Baytril (enroflaxin 0.2 mg/day, i.m. for 10 days) was instituted as needed. All procedures were approved by the Institutional Animal Use and Care Committee at UAMS.

Exercise

One group of rats (Tx only 90D, n=4) underwent no further treatment until reflex testing was carried out 90 days after Tx, while a second group of transected animals (Tx only 30D, n=8) underwent no training but was tested for H-reflex frequency-dependent depression after 30 days, and a group of intact rats served as nontransected controls (CONTROL, n=5). The remaining rats (n=23) were divided into five groups that received MBET daily. Exercise was provided for either 15 days (Tx+Ex 15D, n=5), 30 days (Tx+Ex 30D, n=4), 45 days (Tx+Ex 45D, n=5), 60 days (Tx+Ex 60D, n=5), or 90 days (Tx+Ex 90D, n=4). The exercise regimen MBET involved suspending the rats on a sling with the hindlimbs hanging down and the hind paws strapped to the pedals of a bicycle-type device, which was driven by a motor. The pedaling motion flexed one hindlimb and simultaneously extended the contralateral one, while avoiding overstretching of either limb. Cycling speed was 30 rpm. Exercise sessions consisted of two 30-min episodes with 10 min of rest in between. After the end of the training period, reflex testing was performed. The two Tx only groups also underwent reflex testing 30 days or 90 days after Tx, along with a group of intact rats (CTL), for comparison with the MBET experimental groups.

Reflex Testing

Animals were anesthetized with ketamine (60 mg/kg, i.m.) and maintained with 10% doses as needed such that vibrissal and pinna pinch reflexes were absent. Core body temperature was maintained at 36° C. using a thermostatically controlled heat lamp. A bipolar cuff electrode was placed on the tibial nerve for stimulation (0.1 ms pulses, cathode proximal on nerve). Exposed tissue was covered with mineral oil to prevent drying. A wire electrode was inserted subcutaneously in the digital interosseous muscles between the fourth and fifth metatarsals for EMG recording as previously demonstrated (26, 27), and referenced to a clip applied to the skin on the digits. A ground electrode was attached to the skin of the tail. Recordings were made using amplifier (Grass P511) filter settings of 3 Hz to 3 kHz with the 60 Hz notch filter in use. Responses to the stimulus were digitized and averaged using a GW Instruments (Somerville, Mass., USA) digitizer module and SuperScopeR software.

H- and M-Wave Responses in the Rat

Stimulation of the tibial nerve under the calcaneal tendon produced two responses, an early M-wave (2 ms latency), produced by direct activation of motoneuronal axons in the tibial nerve, and a later H-reflex (8 ms latency), produced by activation of muscle afferents in the tibial nerve, which synapse monosynaptically on plantar motoneurons. The degree of stimulation that induced frequency-dependent depression of the H-reflex was determined. The reflex was first tested at 0.2 Hz to determine threshold and maximal response levels. After discarding the first five responses in order to obtain an average of the stabilized reflex, averages of 10 responses were obtained. Averages were compiled following stimulation at 0.2, 1, 5, and 10 Hz. The change in the response at various frequencies was calculated as the percent of the response at 0.2 Hz in order to determine depression of the H-reflex as a function of stimulation frequency. Following the frequency series testing, the H-reflex amplitude was confirmed at 0.2 Hz for consistency. If the amplitude at recheck was less than 90% of the initial amplitude, the data was discarded.

At the end of the experiment, animals were euthanized with an overdose of barbiturate (Nembutal) and the Tx was confirmed either visually or histologically following transcardial perfusion with paraformaldehyde (4%) and sucrose (20%). Sensory testing or assessment of spasticity was not carried out in this series of animals.

Measurement and Statistics

Figure 1:
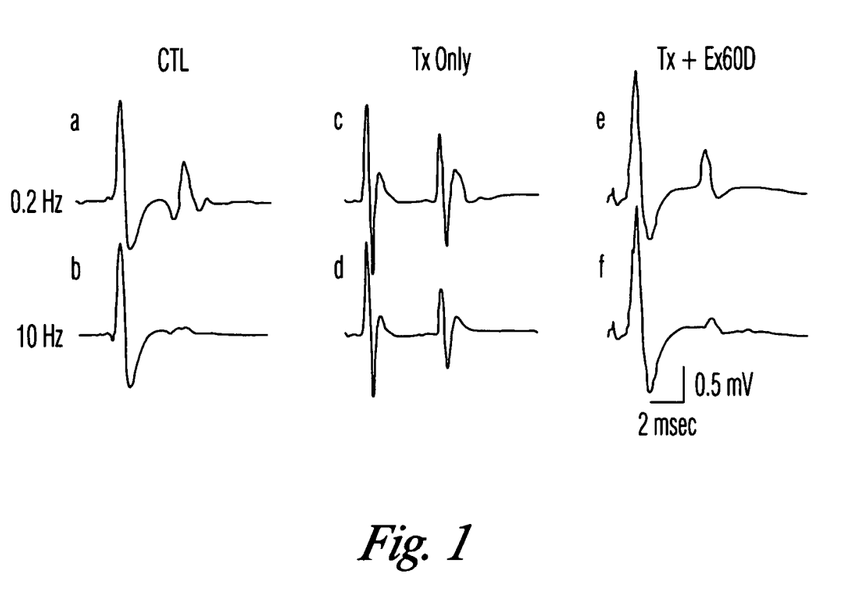

The amplitude of the H-wave was measured from the base line before the H-wave to the peak of the first (and largest) of its two components (FIG. 1). Measurements from peak to peak of the two components gave similar results so that only the baseline to peak measures are reported here. Results from animal groups were compared statistically using a two-way ANOVA test. Significant differences between groups were tested using the Scheffe test, a conservative post hoc comparison. Statistical significance was considered to be present at $P<0.05$.

Results

FIG. 1 panel a, shows representative recordings from an intact CONTROL animal stimulated at 0.2 Hz (the 100% response), along with (FIG. 1, panel b) the response at 10 Hz (group mean±SE of the mean, ~11±4% of the response at 0.2 Hz), and the response from a Tx only 60D rat at 0.2 Hz (100%) (FIG. 1, panel c), and at 10 Hz for comparison (68±6%) (FIG. 1, panel d). Panels e and f of FIG. 1 show the responses from a Tx+Ex 60D rat at 0.2 Hz (100%) and 10 Hz (22±7%), respectively. These recordings demonstrate the main effects of higher frequency stimulation leading to marked frequency-dependent depression in intact animals, of Tx leading to decreased (increased percent) frequency-dependent depression, and of MBET leading to a restoration of frequency-dependent depression of the H-reflex.

Figure 2:
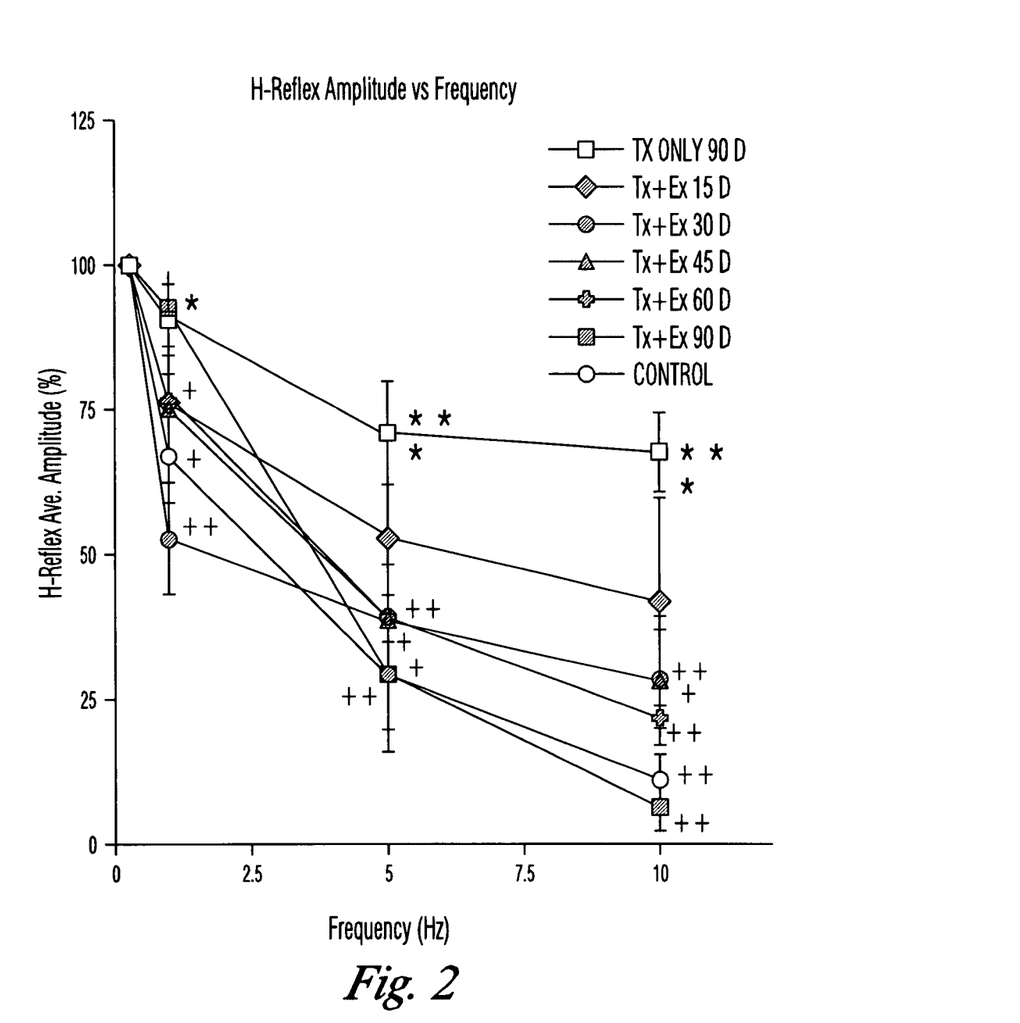

FIG. 2 is a graph of the habituation of the H-reflex following stimulation at 0.2, 1, 5, and 10 Hz in the following groups of animals: Tx only 90D, Tx+Ex 15D, Tx+Ex 30D, Tx+Ex 45D, Tx+Ex 60D, Tx+Ex 90D, and CONTROL. The Tx only 30D) group was not included because of its similarity with the other longer duration unexercised transected group (Tx only 90D). Statistically significant differences between the Tx only 90D group and the other groups at each frequency are denoted by a single (*P<0.05) or a double (**P<0.01) asterisk.

ANOVA of these groups showed statistically significant differences across stimulation frequency (df=3, F=115.11, P<0.001), across experimental groups (df=7, F=6.77, P<0.001), and interaction between frequency and groups (df=21, F=2.17, P<0.008). Post hoc comparisons between all groups were undertaken, and those against the Tx only 90D group were considered the most relevant. When comparing this group with the CONTROL animals, there were no significant differences at 1 Hz, but major differences at 5 Hz (P<0.01) and 10 Hz (P<0.01), indicating decreased frequency-dependent depression (hyper-reflexia) 90 days after Tx. Such decreases in frequency-dependent depression were evident to a similar degree after only 30 days following Tx (Tx only 30D) compared to the CONTROL group (P<0.01), suggesting that hyper-reflexia is manifested within 30 days and remains at similar levels in the chronic (90 day) condition.

The effects of MBET for 15 days (Tx+Ex 15D), while producing a numerical reduction of 15% at each frequency, were not statistically significant. However, after 30 days of MBET (Tx+Ex 30D), there were statistically significant increases in frequency-dependent depression (decreased percent 30+%) at all frequencies tested, indicating that passive exercise led to a restoration of H-reflex habituation. The effects of longer durations of MBET produced decreases in frequency-dependent depression that were variable at the lower frequencies (1 and 5 Hz), but linearly decrementing at 10 Hz. For example, percent frequency-dependent depression decreased from 29% after 30 days (Tx+Ex 30D), to 28% after 45 days (Tx+Ex 45D), to 22% after 60 days (Tx+Ex 60D), to 7% after 90 days (Tx+Ex 90D) of MBET.

Figure 3:
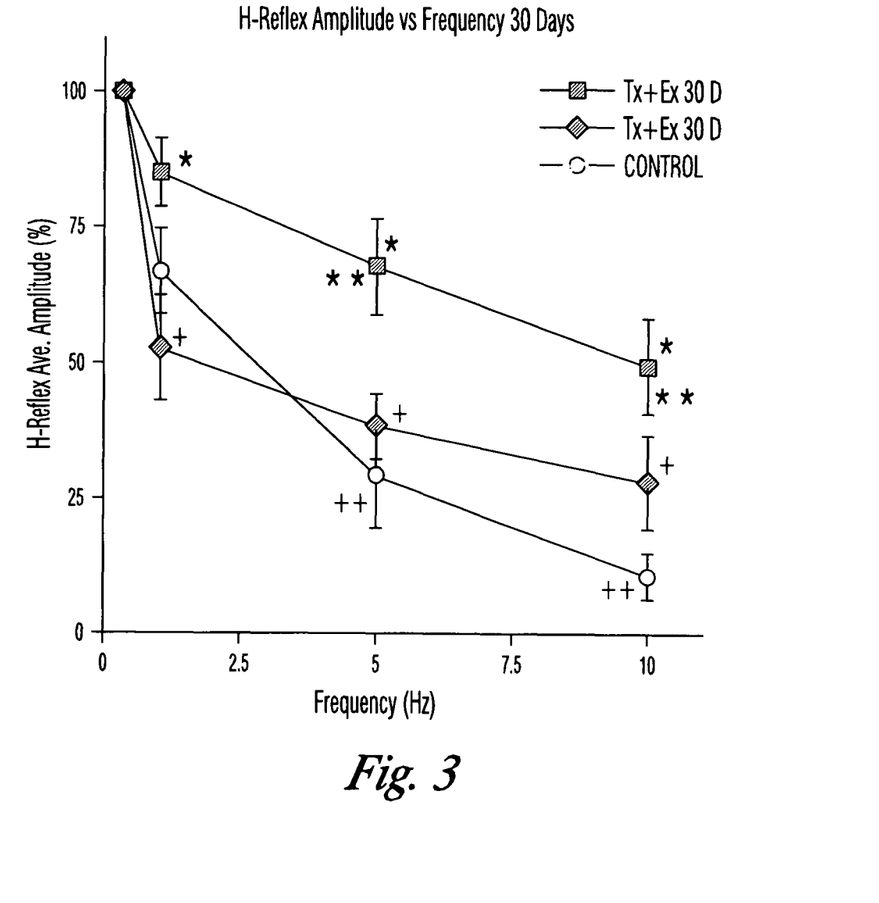

FIG. 3 is a comparison of a delay of 30 days following Tx before testing the H-reflex in untrained rats (Tx only 30D) compared to those trained for 30 days after Tx (Tx+Ex 30D) and to intact animals (CONTROL). Basically, ANOVA shoved a significant difference across groups (df=2, F=12.22, P<0.001) and frequencies (df=3, F=50.46, P<0.001), as well as interaction across these two factors (df=6, F=2.24, P<0.05). Tx only induced statistically significant decreases in frequency-dependent depression at 5 Hz (P<0.01) and 10 Hz (P<0.01) compared to CONTROL (++). MBET for 30 days induced an increase in H-reflex frequency-dependent depression (decreased percent) when comparing the effects of Tx (*P<0.05) to Tx+Ex 30D (+) at both 5 and 10 Hz. These results show that the decrement in low frequency-dependent depression (1-10 Hz) of the H-reflex induced by Tx can be alleviated by MBET in a period as short as 30 days.

Conclusions

This study shows that passive exercise in spinally transected animals can be used to restore low frequency-dependent depression of the H-reflex. The decrement in hyper-reflexia was evident in a MBET duration-dependent manner in Tx rats.

The H-reflex is a reliable measure of spinal circuitry that is altered after an SCI. This reflex normally undergoes changes with a variety of rhythmic motions such as stepping (29), walking (30), running (31), and pedaling (32). In animals, the H-reflex has been a valuable tool to measure changes in spinal circuitry in both contusion (20, 33) and transection models (23, 24). The H-reflex has also been used to assess changes in spinal circuitry in the human, a recent effort concluding that (1) chronically paralyzed subjects showed suppression of H-reflexes to a lesser extent than able-bodied normals or acutely paralyzed subjects, (2) those with acute paralysis showed similar H-reflex suppression as those within 40 weeks of their SCI, but had decreased frequency-dependent depression after 44 weeks of paralysis (i.e., there was marked loss of frequency-dependent depression of the H-reflex in the 'chronic' condition), and (3) changes in muscle fatigue were associated with a decrease in H-reflex suppression over time (13). The results described herein show that frequency-dependent depression of the H-reflex is decreased in the most 'chronic' condition tested, 90 days after Tx. Surprisingly, a similar level of hyper-reflexia was evident even at 30 days (FIG. 3), suggesting that hyper-reflexia assumes a fairly 'chronic' level within 30 days after Tx in the rat. These results are consistent with those of Thompson et al. (20), who reported significantly less frequency-dependent depression of the monosynaptic reflex at 28 and 60 days postinjury in spinal cord contused rats than in normal animals, but this effect was not evident 6 days after injury. Such results suggest that the onset of low frequency-dependent depression of the H-reflex takes weeks to develop. Further studies are required to determine the time course of the decrement in frequency-dependent depression of the H-reflex in the rat.

Other forms of exercise in animal models also show promise in the ability to effect changes in lower limb function following SCI. For example, adult cats showed recovery of full weight-bearing hindlimb stepping on a treadmill within a few weeks following complete spinal transection if treadmill training was implemented (34, 35). Completely spinalized cats that were not treadmill-trained were 3 times less likely to step than those that were trained (36). If spinal cord hemisected rats are immobilized, the expected recovery is delayed and may not be as great (compared to exercised animals) once use is restored (37). We showed that 90 days of MBET minimized loss of muscle mass in transected and exercised, compared to transected only, rats (23, 24). Additionally, we showed that MBET restored frequency-dependent depression of the H-reflex to normal levels in exercised transected rats (24, 25). The H-reflex of nonexercised Tx animals failed to show frequency-dependent depression at most stimulation frequencies.

The present studies were designed to determine the time course of recovery induced by MBET on low frequency-dependent depression of the H-reflex. MBET for only 15 days, while not inducing a statistically significant effect on H-reflex habituation, did have a numerical effect, increasing frequency-dependent depression (decreasing percent inhibition) at 10 Hz from 69 to about 42%. MBET for 30, 45, and 60 days induced a similar, significant reduction in percent inhibition from 69 to around 22-29%. Not until 90 days of MBET was there a further reduction to around 7%. These findings suggest that MBET had a fairly rapid ameliorative effect on H-reflex frequency-dependent depression, and could have added effects if continued long term.

Section 2

Use of a Motorized Bicycle Exercise Trainer to Normalize Frequency-Dependent Habituation of the H-Reflex in Spinal Cord Injury In an animal model in Section 1 of this Example, exercise on a motor-driven bicycle was shown to normalize hyperactivity of the H-reflex in plantar muscles of rats after complete spinal cord transection at the T10 level. This study was conducted to test the effect of a similar exercise program in humans with an SCI on the habituation of the H reflex to assess hyper-reflexia, a component of spasticity and an indirect assessment of spasticity.

Methods

The participant was a 24-year-old male with ASIA B C7 SCI due to a gunshot wound thirteen months prior to the start of this study. His post-injury rehabilitation was complicated by neuropathic pain in the right upper extremity which was mitigated the use of Neurontin, and was subsequently discharged to live with his parents. Spasticity was a problem for him, which he was managing with routine stretches. He wanted to avoid aggressive management with either oral or intrathecal medication. Prior to starting the exercise program, a D-Dimer blood test indicated a low risk of a deep vein thrombosis (DVT) and a venous Doppler ultrasound exam was not required. His risk of osteoporosis was assessed with a standard DEXA scan. The participant's Z score at the femoral neck was −2.8, and risk of fracture was discussed prior to starting the exercise program. The risk and benefits were discussed with him and he signed an informed consent form approved by the IRB at UAMS prior to the start of the study. He was passively exercised 5 days a week for 13 weeks on a motorized bicycle exercise trainer designed for the purpose at the University of Arkansas for Medical Sciences. He performed the exercises from his wheelchair with feet secured to the pedals. The first week was started at a slower speed, approximately 20 cycles per minute (cpm), but by the second week he was exercising at 40 cpm for 30 minutes with a 10 minute break and then another 30 minutes. H-reflex habituation was assessed prior to the exercise session with the subject prone with knee slightly flexed and the ankle in 0 degree dorsiflexion. The frequency range tested was 0.2, 1, 5, and 10 Hz. The stimulating electrode (all electrodes disposable type, Nicloet Biomedical, Inc.) was positioned over the right Tibial nerve at the level of the popliteal fossa, and the recording electrode over the right Soleus muscle with the reference electrode over the right Achilles tendon. A ground electrode was placed over the right tibial crest. After discarding the first five trials, tent H-reflexes were averaged at each frequency tested. The amplitude of the H-reflex was computed as a percentage of that recorded at low frequency (0.2 Hz), which was considered to be 100%. This study was approved by the Institutional Review Board at the University of Arkansas for Medical Sciences.

Results

Figure 4:
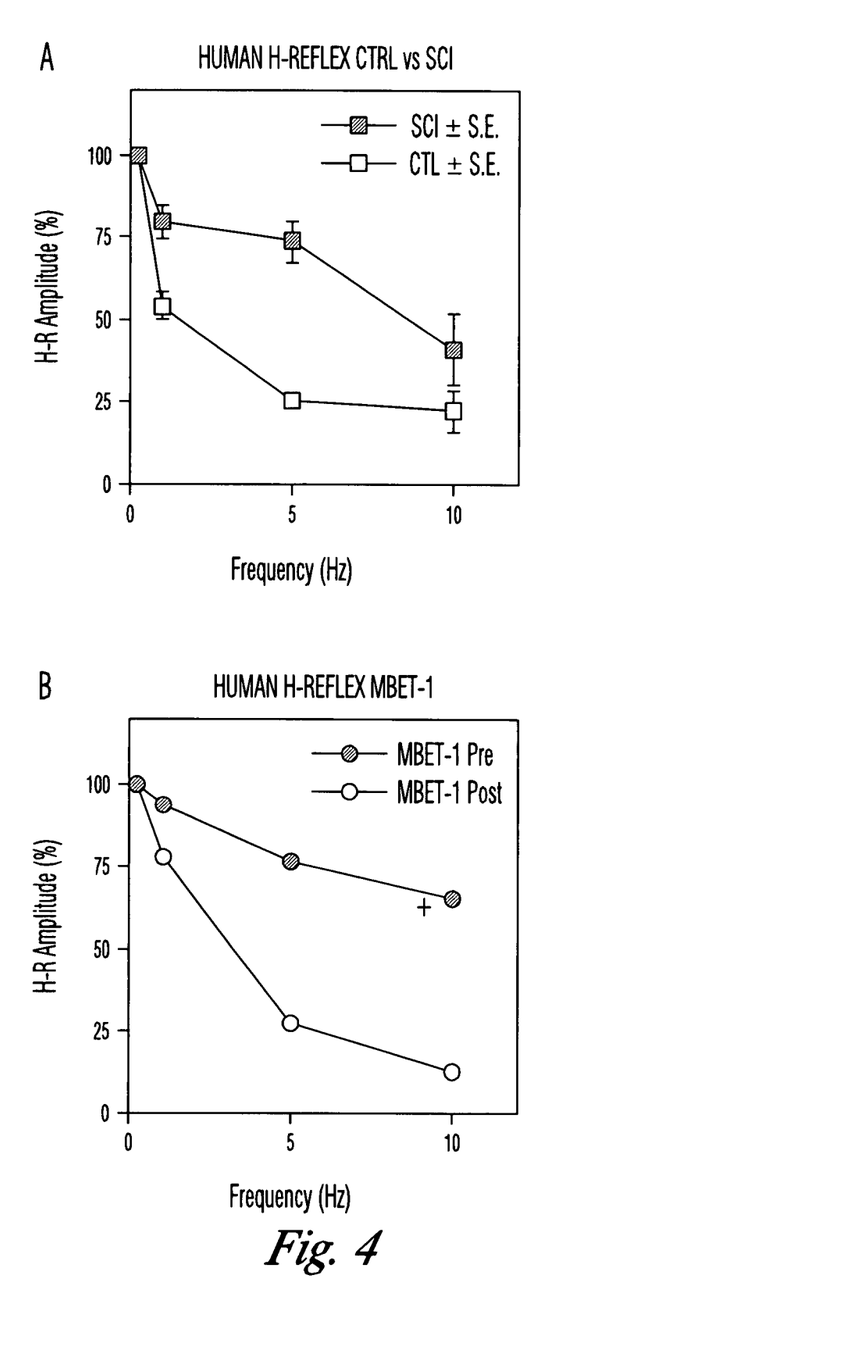
Figure 5:
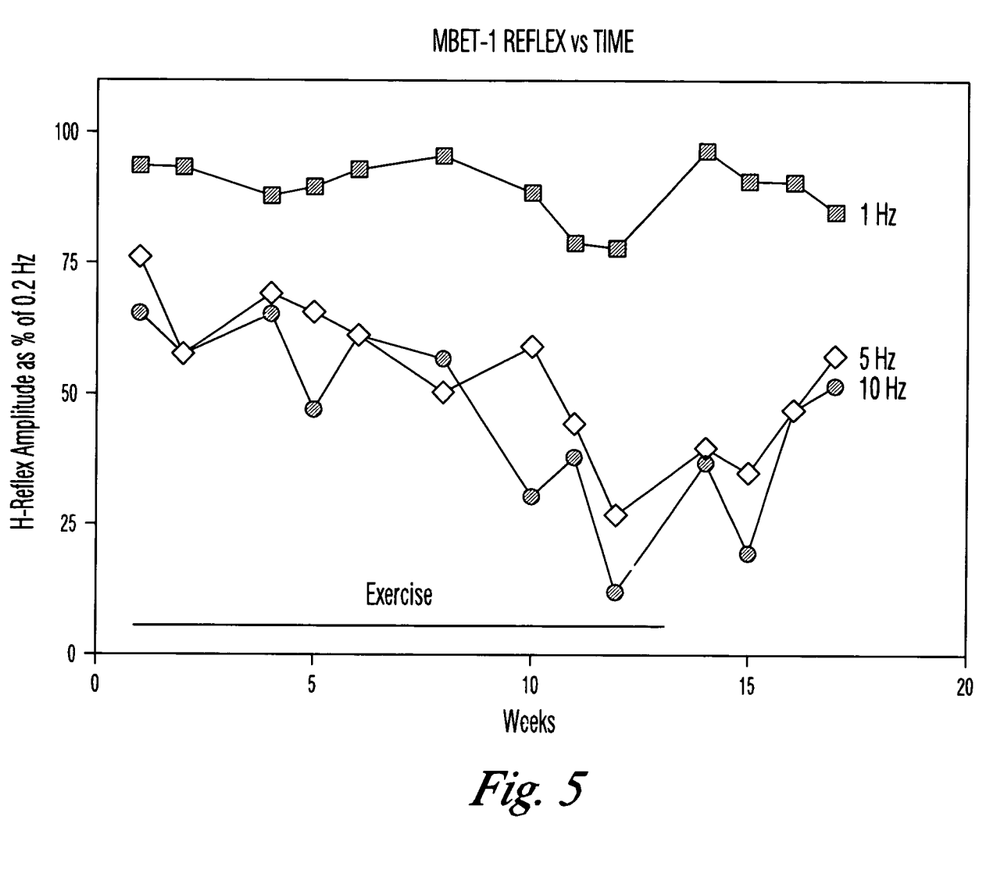

FIG. 4, panel A shows H-reflex testing on 16 normal controls and 6 SCI victims. These two groups were statistically significantly different (Two-way ANOVA, $F_{1,19}=21.2$, $p<0.0001$) and the Nwhan-Keuls post-hoc test showed a statistically significant difference in low frequency H-reflex habituation at 5 Hz ($p>0.01$). Recordings from the present subject (FIG. 4, panel B) show the habituation profile for the tested frequencies before MBET (MBET-1 PRE) and after 12 weeks of MBET (MBET-1 POST). Note that this subject's habituation at both 5 Hz and, especially, 10 Hz before the MBET treatment was at a higher percentage than average for the other SCI patients. FIG. 5 shows the results of H-reflex testing in the present subject throughout the testing period. Initially, H-reflex amplitude at 5 Hz was 76% and at 10 Hz 65%, consistent with a hyperactive spastic muscle. After 8 weeks, the amplitude began to decrease and at 12 weeks had decreased to 27% at 5 Hz and 12% at 10 Hz (comparable to normal controls). Exercise was stopped at 13 weeks, but the subject's H-reflex was reassessed weekly for four weeks. The amplitude of the H-reflex remained at near normal levels for two weeks after exercise ceasing, but by 17 weeks the H-reflex at 5 Hz at increased to 57% and at 10 Hz to 52%, indicating a rapid return of the subject's spasticity. A linear component was used to test differences in frequency-dependent H-reflex amplitudes between early and late times in the exercise and testing period. In weeks 1-6 the average response was 66±7% compared to 38±8% in weeks 10-15. These average values of H-reflex amplitudes are significantly different (Student's t-test, $t=5.70$, $p<0.0009$). Similarly, at 10 Hz the average H-reflex amplitude in weeks 1-6 was 59±11% in weeks 10-15 ($t=5.21$, $p<0.002$). These differences indicate the effectiveness of MBET exercise in normalizing the frequency-dependent amplitude of the H-reflex. This subject also reported reduced spasticity at the end of the training regiment, as would be expected due to the normalization of reflexes.

Section 3

Modafinil Restored Frequency Dependent Depression of the H-Reflex in Spinally Transected Rats Methods:

Rats were spinally transected as in Section 1 of this Example. One group of rats received no exercise after transection. A second group of rats was treated with passive exercise using the motorized bicycle exercise trainer, as in Section 1. Passive exercise was begun within 7 days of transection. A third group of transected rats were not exercised but were given 3 mg/Kg modafinil per day. A 100 mg modafinil pill was ground by mortar and pestle and mixed with 9 ml of syrup and 1 ml of water. The dose to the animal was 0.1 ml p.o. daily (3 mg/Kg/day). Modafinil was started between 48 hours and 7 days after transection. A fourth group of rats was untransected normal controls. Each group contained 9 to 12 rats.

At 30 days after transection, the H-reflex of each rat was measured as in Section 1.

Figure 6:
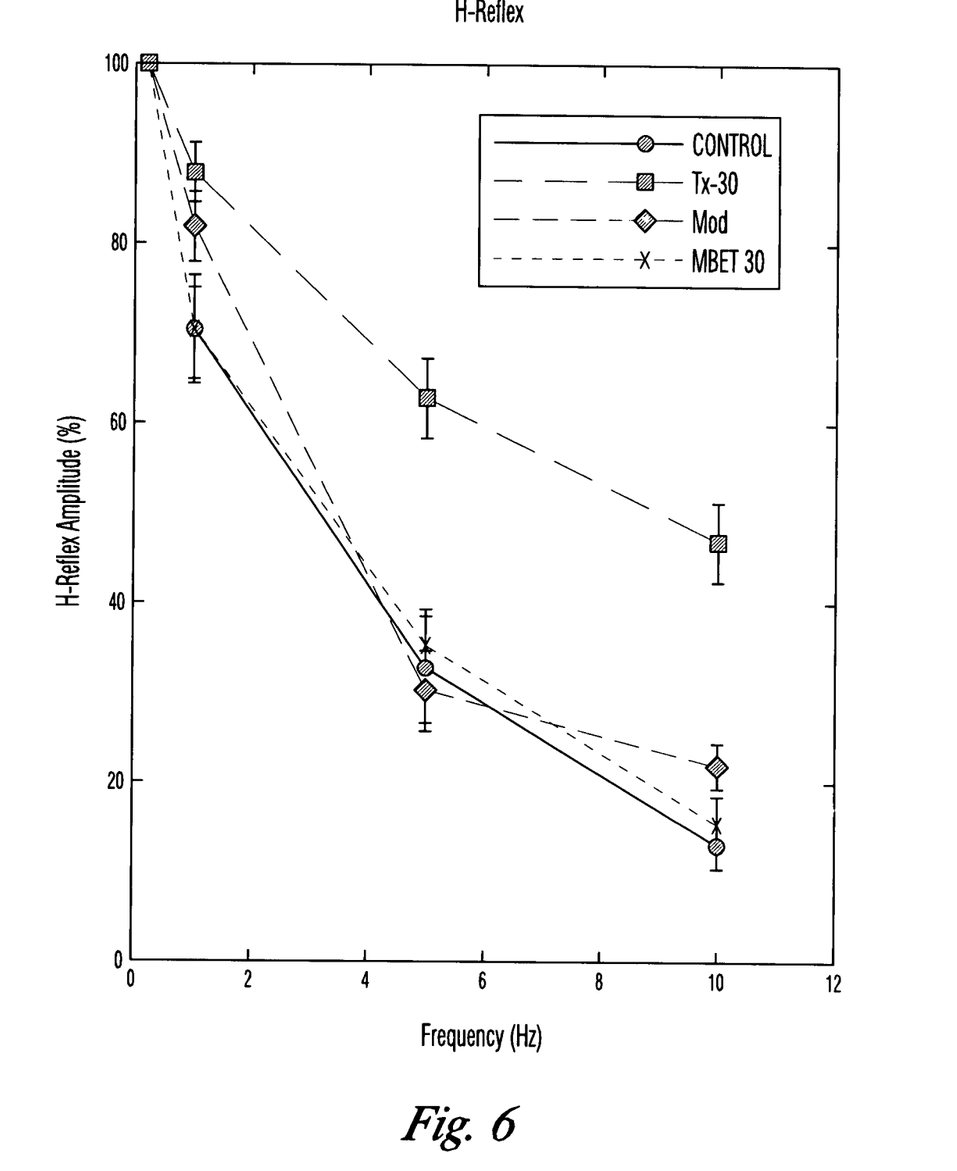
FIG. 6. Averages of H-reflex recordings in intact, spinal cord injured, spinal cord injured and exercised, and spinal cord injured and modafinil-treated rats. Plot of H-reflex amplitude at stimulation frequencies from 0.2 to 10 Hz for normal rats (control), spinalized rats 30 days after spinal transection given no treatment (Tx–30), spinalized rats treated with passive exercise using a motorized bicycle trainer for 30 days after spinal transection (MBET-30), and spinalized rats treated with modafinil for 30 days after spinal transection (Mod). These results show that modafinil alone was as effective as passive exercise in normalizing exaggerated reflexes in spinal transected rats.

Results:

The H-reflex of the four groups of rats was measured at 30 days after transection at stimulation frequencies from 0.2 to 10 Hz. The four groups of rats were normal controls (control), transected and untreated for 30 days after transection (Tx–30), transected and treated solely with 3 mg/Kg/day modafinil p.o. for 30 days (Mod), and transected and treated solely with passive exercise for 30 days (MBET 30). The results are shown in FIG. D1.

FIG. 6 shows that as you increase the stimulation for 0.2 to 10 Hz, the H-reflex amplitude in intact rats (control) decreases markedly. In rats that were transected and tested 30 days after surgery (Tx–30), the amplitude of the reflex did not habituate—that is, there was hyper-reflexia. In rats that were transected and MBET begun within 7 days after surgery and exercised for 30 days (MBET 30), the reflex amplitude decreased as in intact animals, indicating that passive exercise led to a normalization of the hyper-reflexia. In animals that were transected and not exercised but given daily doses of modafinil beginning 7 days after surgery (Mod), the reflexes were normalized, indicating that modafinil also alleviated hyper-reflexia.

Hyper-reflexia is a component of spasticity, so that normalization of hyper-reflexia indicates a reduction or elimination of spasticity. These studies demonstrated that oral administration of modafinil, which is used to promote waking in narcoleptic subjects, was effective in reducing hyper-reflexia after spinal transection

Section 4

Changes in Connexin 36 mRNA in Spinalized Rats

A Novel Molecular Mechanism for Hyper-Reflexia.

Figure 7:
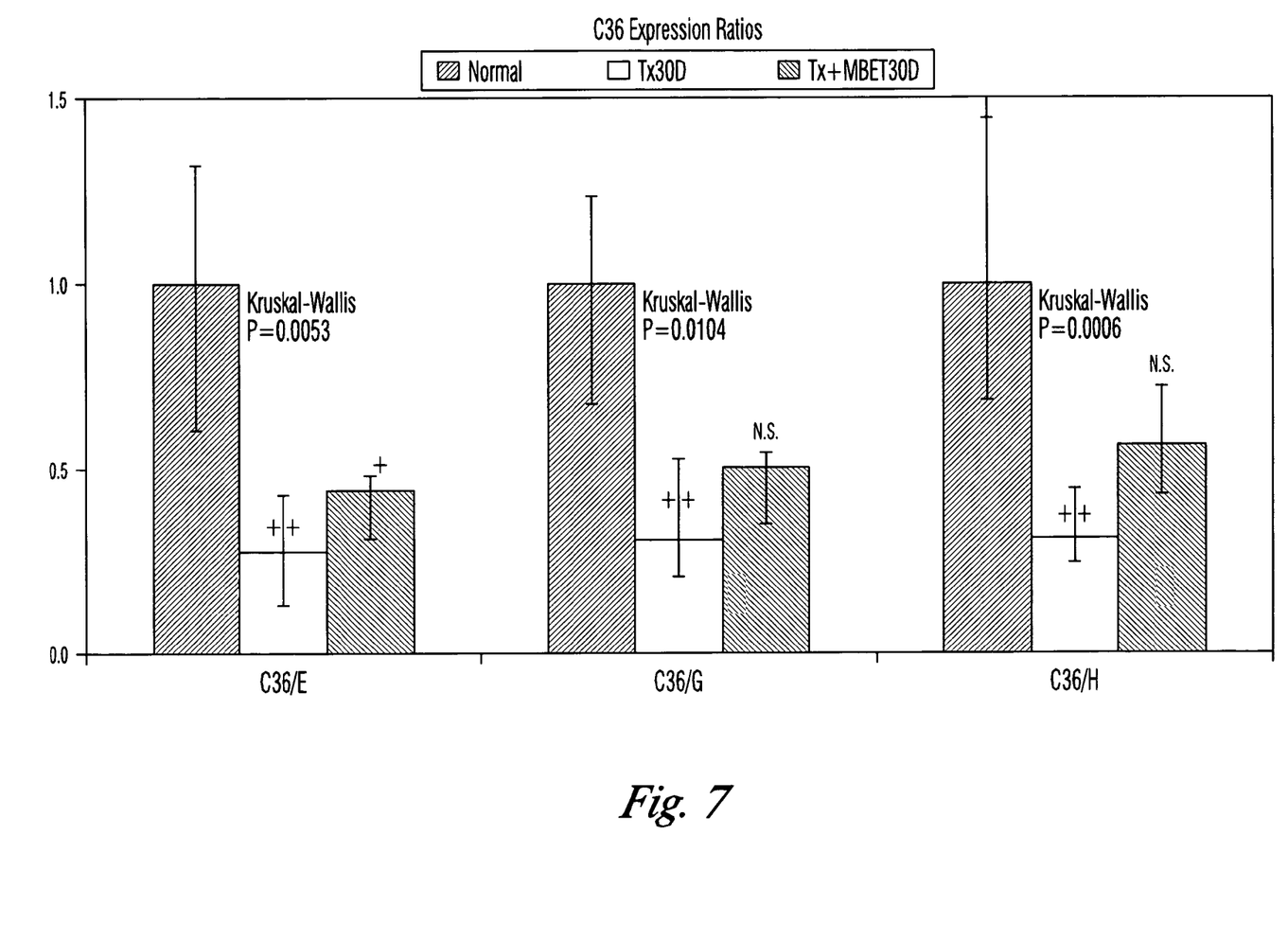

We reasoned that a delay of weeks to months in the onset of hyper-reflexia and spasticity indicated that a mechanism involving protein expression may be at play. If changes in presynaptic inhibition were really responsible for hyper-reflexia and spasticity, their onset would be immediate after injury, not delayed. We also reasoned that, following a spinal cord lesion, the tissue below the level of the lesion would regress to a neonatal state. A major change in development is the change in electrical coupling between motoneurons. In the developing rat spinal cord, motoneurons are electrically coupled until about 7 days of life, but coupling disappears by 14 days of life (52). Electrical coupling in neurons depends on gap junctions, specifically, the gap junction protein connexin 36 (Cx36) (53). We used RT-PCR to detect changes in Cx36 expression after Tx. We sampled spinal cord tissue below the level of the transection after testing the H-reflex. FIG. 7 shows that Cx36 expression decreased dramatically by 30 days after Tx (Tx30D) compared to intact rats (Normal). In rats that had 30 days of MBET after transection (Tx+MBET30D), Cx36 expression increased significantly above the 30 day Tx only rats. This suggests that Cx36 expression a) decreased after Tx, and b) increased towards the levels in intact animals after Tx+MBET. These results suggest that, following Tx, motoneurons may become electrically uncoupled due to decreases in gap junctions after injury. MBET, perhaps by inducing alternation in both limbs simultaneously, thereby mimicking bipedal locomotion, may lead to recoupling of motoneurons leading to coordinated activation, rather than independent activation, of motor units, which is facilitated by an increase in gap junctions.

Conclusion

These results suggest that changes in Cx36 levels in spinal cord tissue, in response to Tx, could play a role in the development of hyper-reflexia and spasticity.

Since we suspected that gap junctions may be involved in the manifestation of hyper-reflexia, we reasoned that an agent that would increase electrical coupling in neurons might be useful for the treatment of hyper-reflexia, the main component of spasticity. Recent unpublished evidence from Rodolfo Llinas at New York University suggests that modafinil increases electrical coupling in cortical cells, inferior olivary cells and thalamic reticular cells (personal communication). We reasoned that modafinil could increase electrical coupling in spinal cord neurons, and so began the study described above using modafinil as a potential treatment for hyper-reflexia.

In summary, the previously unknown mechanism of action of modafinil may be to increase electrical coupling in brain cells involved in waking, making it effective for the treatment of narcolepsy. Such a mechanism has never before been proposed but will be published soon by the Llinas laboratory. Since we discovered that hyper-reflexia, the main component of spasticity, might be due to a decrease in gap junction expression and a concomitant decrease in electrical coupling, then we reasoned that modafinil may be useful for the treatment of spasticity by potentially increasing gap junction protein expression of Cx36, just as passive exercise did.

REFERENCES

1. Magladery J W, Teasdall R D, Park A M, Languth H W. Electrophysiological studies of reflex activity in patients with lesions of the nervous system. I. A comparison of spinal motoneurone excitability following afferent nerve volleys in normal persons and patients with upper motor neurone lesions. Bull Johns Hopk Hosp 1952; 91: 219-244.
2. Milanov I. Examination of the segmental pathophysiological mechanisms of spasticity. Electromyogr Clin Neurophysiol 1994; 34: 73-79.
3. Laudau W M, Clare M H. Fusimotor function. VI. H-reflex, tendon jerk and reinforcement in hemiplegia. Arch Neurol Psychiat 1964; 10: 128-134.
4. Bennett D J, Li Y, Harvey P J, Gorassini M. Evidence for plateau potentials in tail motoneurons of awake chronic spinal rats with spasticity. J Neurophysiol 2001; 86: 1972-1982.
5. Eken T, Hultborn H, Kiehn G. Possible functions of transmitter-controlled plateau potentials in alpha motoneurons. Prog Brain Res 1989; 80: 257-267.
6. Li Y, Bennett D J. Persistent sodium and calcium currents cause plateau potentials in motoneruons of chronic spinal rats. J Neurophysiol 2003; 90: 857-869.
7. Li Y, Li X, Harvey P J, Bennett D J. Effects of baclofen on spinal reflexes and persistent inward currents in motoneurons of chronic spinal rats with spasticity. J Neurophysiol 2004; 92: 2694-2703.
8. Hultborn H. Changes in neuronal properties and spinal reflexes during development of spasticity following spinal cord lesions and stroke: studies in animal models and patients. J Rehab Med 2003; S41: 46-55.
9. Nielsen J, Petersen N, Crone C. Changes in transmission across synapses of Ia afferents in spastic patients. Brain 1995; 118: 995-1004.
10. Little J W, Ditunno J F, Steins S A, Harris R M. Incomplete spinal cord injury: neuronal mechanisms of motor recovery and hyperreflexia. Arch Phys Med Rehab 1999; 80: 587-599.
11. Kitzman P. Alteration in axial motoneuronal morphology in the spinal cord injured spastic rat. Exper Neurol 2005; 192: 100-108.
12. Calancie B et al. Evidence that alterations in presynaptic inhibition contribute to segmental hypo- and hyperexcitability after spinal cord injury in man. Electroencephalogr and Clin Neurophysiol 1993; 89: 177-186.
13. Schindler-Ivens S, Shields R K. Low frequency depression of H-reflexes in humans with acute and chronic spinal-cord injury. Exp Brain Res 2000; 133: 233-241.
14. Pierrot-Deseilligny P. Electrophysiological assessment of the spinal mechanisms underlying spasticity. New Trends Adv Tech Clin Neurophysiol 1990; 41: 264-273.
15. Faist M, Mazevet D, Dietz V, Pierrot-Deseilligny E. A quantitative assessment of presynaptic inhibition of Ia afferents in spastics: differences in hemiplegics and paraplegics. Brain 1994; 117: 1449-1455.
16. Angel R W, Hofmann W W. The H-reflex in normal, spastic, and rigid subjects. Arch Neurol 1963; 8: 591-596.
17. Little J W, Halar E M. H-reflex changes following spinal cord injury. Arch Phys Med Rehab 1985; 66: 19-22.
18. Olsen P Z, Diamantopoulos E. Excitabiliity of spinal motor neurons in normal subjects and patients with spasticity, Parkinsonian rigidity, and cerebellar hypotonia. J Neurol Neurosurg Psychiatry 1967; 30: 325-331.
19. Yablon S A, Stokic D S. Neurophysiologic evaluation of spastic hypertonia. Am J Phys Med Rehab 2004; 83: S10-S18.
20. Thompson F J, Reier P J, Lucas C C, Parme R. Altered patterns of reflex excitability subsequent to contusion injury of the rat spinal cord. J Neurophysiol 1992; 68: 1473-1486.

21. Chen X Y, Feng-Chen K C, Chen L, Stark D M, Wolpaw J R. Short-term and medium-term effects of spinal cord tract transactions on soleus H-reflex in freely moving rats. J Neurotrauma 2001; 18: 313-327.
22. Ishikawa K, Ott K, Porter R W, Stuart D. Low frequency depression of the H wave in normal and spinal man. Exp Neurol 1966; 15: 140-156.
23. Reese N B et al. Restoration of H-reflex habituation by passive exercise in spinally transected rats. American Phys Ther Assoc Combined Sections Meeting. Nashville, Tenn. 2004.
24. Skinner R D, Houle J D, Reese N B, Berry C L, Garcia-Rill E. Effects of exercise and fetal spinal cord implants on the H-reflex in chronically spinalized adult rats. Brain Res 1996; 729: 127-131.
25. Skinner R D, Houle J D, Reese N B, Dempster J, Garcia-Rill E. Amelioration of the H-reflex in chronically spinalized adult rats by exercise and fetal spinal cord implants. Soc Neurosci Abst 1998; 24: 2103.
26. Meinck H M. Occurrence of the H-reflex and the F wave in the rat. Electroencephalogr Clin Neurophysiol 1976; 41: 530-533.
27. Cliffer K D et al. Consistent repeated M- and H-wave recording in the hind limb of rats. Muscle Nerve 1998; 21: 1405-1413.
28. Dachy B, Dan B. Electrophysiological assessment of the effect of intrathecal baclofen in spastic children. Clin Neurophysiol. 2002; 113(3):336-40.
29. Crenna P, Frigo C. Excitability of the soleus H reflex arc during walking and stepping in man. Exp Brain Res 1978; 66: 49-60.
30. Brooke J D, Collins D F, Boucher S, McIlroy W. Modulation of human short latency reflexes between standing and walking. Brain Res 1991; 548: 172-178.
31. Capaday C, Stein R B. Difference in the amplitude of the human soleus H-reflex in walking and running. J Physiol 1987; 392: 513-522.
32. Brooke J D, McIlroy W E, Collins D F. Movement and H reflex modulation. I. Pedalling versus matched controls. Brain Res 1992; 582: 78-84.
33. Thompson F J, Parmer R, Reier P J. Alteration in rate modulation of reflexes to lumbar motoneurons after mid thoracic spinal cord injury in the rat. I. Contusion Injury. J Neurotrauma 1998; 15: 495-508.
34. Barbeau H, Rossignol S. Recovery of locomotion after chronic spinalization in the adult cat. Brain Res 1987; 412: 84-95.
35. Lovely R G, Gregor R G, Roy R R, Edgerton V R. Effects of training on the recovery of full-weight-bearing stepping in the adult spinal cat. Exp Neurol 1986; 92: 421-435.
36. de Leon R D, Hodgson J A, Roy R R, Edgerton V R. Locomotor capacity attributable to step training versus spontaneous recovery after spinalization in adult cats. J Neurophysiol 1998; 79:1329-1340.
37. Little J W, Harris R M, Lerner S J. Immobilization impairs recovery after spinal cord injury. Arch Phys Med Rehab 1991; 72: 408-412.
38. Trimble M H, Kukulka C G, Behrman A L. The effect of treadmill gait training on low-frequency depression of the soleus H-reflex: comparison of a spinal cord injured man to normal subjects. Neurosci Lett 1998; 246: 186-188.
39. Houle J D, Morris K, Skinner R D, Garcia-Rill E, Peterson C. Effects of fetal spinal cord tissue transplants and cycling exercise on the soleus muscle in spinalized rats. Muscle Nerve 1999; 22: 846-856.
40. Pizzi A, Carlucci G, Falsini C, Verdesca S, Grippo A. Evaluation of upper-limb spasticity after stroke: A clinical and neurophysiologic study. Arch Phys Med Rehabil. 2005; 86(3):410-5.
41. Bakheit A M, Maynard V A, Curnow J, Hudson N, Kodapala S. The relation between Ashworth scale scores and the excitability of the alpha motor neurones in patients with post-stroke muscle spasticity. J Neurol Neurosurg Psychiatry. 2003; 74(5):646-8.
42. Walton K D, Navarrete R. Postnatal changes in motoneurone electrotonic coupling studied in the in vitro rat lumbar spinal cord. J Physiol 1991; 433: 283-305. |PubMed|ISI|ChemPort|
43. Katz R, Rymer W. Spastic hypertonia: mechanisms and measurement. Arch Phys Med Rehabil 1989; 70: 144-155.
44. Eriksson J, Olausson B, Jankowska E. Antispastic effects of L-dopa. Exp Brain Res 1996; 111: 296-304.
45. Benz E N, Hornby T G, Bode R K, Scheidt R A, Schmit B D. A physiologically based clinical measure for spastic reflexes in spinal cord injury. Arch Phys Med Rehab 2005; 86: 52-59.
46. Wernig A, Nanassy A, Muller S. Laufband (LB) therapy in spinal cord lesioned persons. Prog Brain Res 2000; 128: 89-97.
47. Wirz M, Colombo G, Dietz V. Long term effects of locomotor training in spinal humans. J Neurol Neurosurg Psychiatry 2001; 71: 93-96.
48. Sadowsky C L. Electrical stimulation in spinal cord injury. Neurorehabilitation 2001; 16: 165-169.
49. Wieler M et al. Multicenter evaluation of electrical stimulation systems for walking. Arch Phys Med Rehab 1999; 80: 495-500.
50. Barbeau H, Norman K E. The effect of noradrenergic damage on the recovery of walking after spinal cord injury. Spinal Cord 2003; 41: 137-143.
51. Dietz V, Miller R, Colomb G. Locomotor activity in spinal man: significance of afferent input from joint and load receptors. Brain 2002; 125:2626-2634.
52. Walton K D, Navarrete R. Postnatal changes in motoneurone electrotonic coupling studied in the in vitro rat lumbar cord. J Physiol 1991; 433: 283-305.
53. Chang Q, Gonzalez M Pinter M J, Balice-Gordon R J. Gap junctional coupling and patterns of connexin expression among neonatal rat lumbar spinal motor neurons. J Neurosci 1999; 19: 10813-10828.

All patents, patent applications, and other references cited are incorporated by reference.

What is claimed is:
1. A method of treating spasticity in a mammal comprising: administering to the mammal a dose of a compound of formula I effective to reduce hyper-reflexia in the mammal;

wherein each of rings a and b may optionally be substituted by one or more of the groups F, Cl, Br, $CF_3$, $NO_2$, $NH_2$, $C_{1-4}$alkyl, $C_{1-4}$alkoxy, and methylenedioxy;

Z is >CHSO; and

A is hydrogen; $C_{1-4}$alkyl; $C_{1-4}$hydroxyalkyl; a group of the formula —Y—$NR_2$, wherein Y is a divalent linear or branched chain $C_{1-4}$hydrocarbon radical and each R is independently H or $C_{1-4}$alkyl;

and pharmaceutically acceptable salts thereof;

wherein the spasticity is not secondary to cerebral palsy.

2. The method of claim 1 wherein the spasticity is secondary to multiple sclerosis, a spinal cord injury, a stroke, or a brain injury.

3. The method of claim 1 wherein the spasticity is secondary to a spinal cord injury.

4. The method of claim 1 wherein the compound of formula I is modafinil.

5. The method of claim 1 wherein in the compound of formula I, Z is >CH—SO—.

6. The method of claim 1 wherein in the compound of formula I, A is hydrogen, hydroxymethyl or β-morpholinoethyl.

7. The method of claim 1 wherein the spasticity is secondary to multiple sclerosis.

8. The method of claim 3 wherein the method comprises beginning administering to the mammal a dose of a compound of formula I after the spinal cord injury and before spasticity develops.

9. The method of claim 3 wherein the method comprises beginning administering to the mammal a dose of a compound of formula I within 4 weeks after the spinal cord injury.

10. The method of claim 1 wherein the spasticity is secondary to a spinal cord injury, a stroke, or a brain injury, wherein the method comprises beginning administering to the mammal a dose of a compound of formula I after the spinal cord injury, stroke, or brain injury, and before spasticity develops.

11. The method of claim 1 wherein the spasticity is secondary to a spinal cord injury, a stroke, or a brain injury, wherein the method comprises beginning administering to the mammal a dose of a compound of formula I within 4 weeks after the spinal cord injury, stroke, or brain injury.

12. The method of claim 1 wherein the spasticity is secondary to multiple sclerosis, wherein the method comprises beginning administering to the mammal a dose of a compound of formula I after a diagnosis of multiple sclerosis and before spasticity develops.

13. The method of claim 1 wherein administering the dose of the compound of formula I is effective to increase connexin 36 levels in spinal cord neurons.

14. The method of claim 1 wherein administering the dose of the compound of formula I is effective to increase gap junctions in neurons in the spinal cord.

15. The method of claim 1 wherein administering the dose of the compound of formula I is effective to increase electrical coupling between neurons in the spinal cord.

* * * * *